(12) United States Patent
Boustie et al.

(10) Patent No.: US 9,265,706 B2
(45) Date of Patent: Feb. 23, 2016

(54) LICHESTERINIC ACID AND THE DERIVATIVES OF SAME AS PIGMENTATION INHIBITORS

(71) Applicants: Centre National de la Recherche Scientifique—CNRS, Paris (FR); Universite de Rennes 1, Rennes (FR); Centre Hospitalier Universitaire Pontchaillou, Rennes (FR)

(72) Inventors: Joel Boustie, Montgermont (FR); Marie-Dominique Galibert-Anne, Rennes (FR); Francoise Lohezic-le Devehat, Orgeres (FR); Marylene Chollet-Krugler, La Chapelle Chaussee (FR); Sophie Tomasi, Rennes (FR); Nicolas Mouchet, Vitre (FR); Beatrice Legouin-Gardadennec, Treffendel (FR)

(73) Assignees: Centre National de la Recherche Scientifique—CNRS, Paris (FR); Universite de Rennes 1, Rennes (FR); Centre Hospitalier Universitaire Pontchaillou, Rennes (FR)

( * ) Notice: Subject to any disclaimer, the term of this patent is extended or adjusted under 35 U.S.C. 154(b) by 0 days.

(21) Appl. No.: 14/395,169

(22) PCT Filed: Apr. 18, 2013

(86) PCT No.: PCT/FR2013/050856
§ 371 (c)(1),
(2) Date: Oct. 17, 2014

(87) PCT Pub. No.: WO2013/156738
PCT Pub. Date: Oct. 24, 2013

(65) Prior Publication Data
US 2015/0105459 A1    Apr. 16, 2015

(30) Foreign Application Priority Data
Apr. 18, 2012    (FR) ...................................... 12 53585

(51) Int. Cl.
| | |
|---|---|
| C07D 307/00 | (2006.01) |
| A01N 43/08 | (2006.01) |
| A61K 8/49 | (2006.01) |
| A61Q 19/02 | (2006.01) |
| C07D 307/68 | (2006.01) |
| A61K 31/365 | (2006.01) |

(52) U.S. Cl.
CPC ............. *A61K 8/4973* (2013.01); *A61K 31/365* (2013.01); *A61Q 19/02* (2013.01); *C07D 307/68* (2013.01)

(58) Field of Classification Search
CPC ...................................................... A61K 31/341
USPC .................................. 549/322, 323; 514/473
See application file for complete search history.

(56) References Cited

U.S. PATENT DOCUMENTS

2011/0212194 A1    9/2011    Wang et al.

FOREIGN PATENT DOCUMENTS

FR    2957078    9/2011

OTHER PUBLICATIONS

Cavaltto et al. J. Am. Chem. Soc. 1948, 70(11), 3724-3726.*
Abrahams et al., "Lichen-derived compounds, lichesterinic and photolichesterinic acids, mediate pigmentation," http://www.aferp.univ-rennes1.fr/aferp nouveau/athens/poster/PB170-Rennes%20(2).pdf [retrieved on Jul. 25, 2012] XP002680662.
International Search Report and Written Opinion in PCT/FR2013/050856 dated Oct. 14, 2013.
Katagiri et al., "Skin external agent contg. lichesteric acid has high melanism-inhibiting effect enabling treatment of pigmentation and whitening of skin" (1993) XP002680663.

* cited by examiner

*Primary Examiner* — Nizal Chandrakumar
(74) *Attorney, Agent, or Firm* — McAndrews, Held & Malloy Ltd.; Nabeela Rasheed

(57) ABSTRACT

The invention relates to the cosmetic use of a compound chosen from the compounds of formula (A) and the salts of same as an agent for depigmenting the skin and/or keratinous appendages.

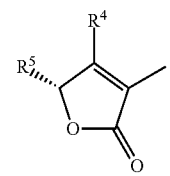

(A)

2 Claims, 2 Drawing Sheets

LICHESTERINIC ACID AND THE DERIVATIVES OF SAME AS PIGMENTATION INHIBITORS

Figure 1:
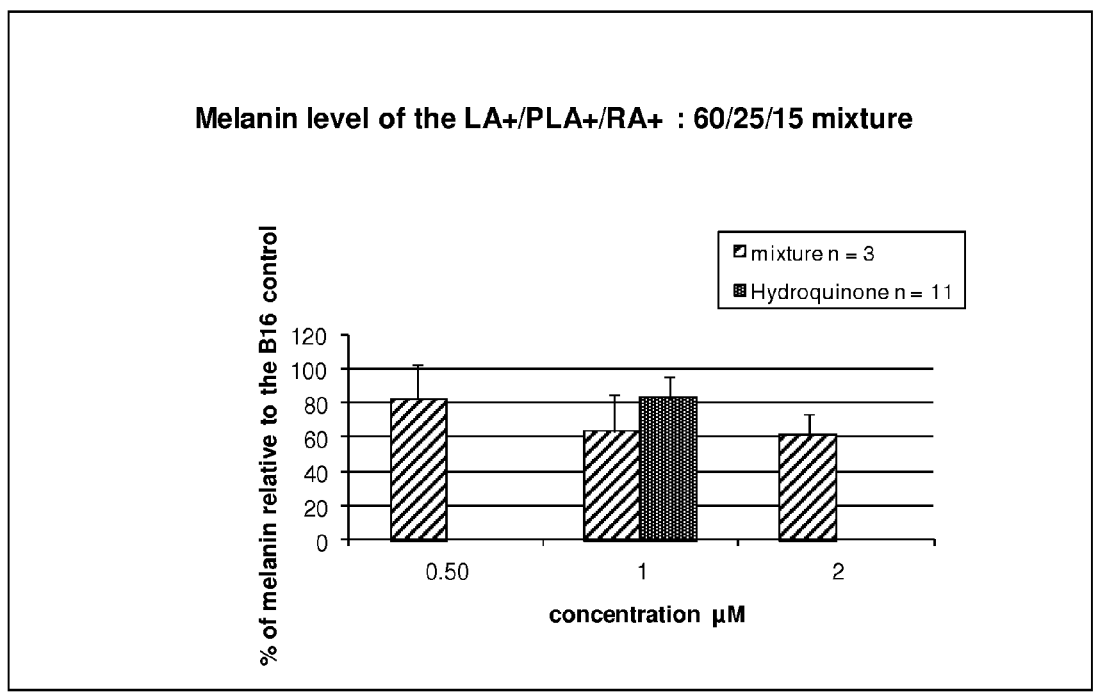

The present application is filed pursuant to 35 U.S.C. 371 as a U.S. National Phase application of International Patent Application No. PCT/FR2013/050856, which was filed Apr. 18, 2013, claiming the benefit of priority to French Patent Application No. 1253585, which was filed on Apr. 18, 2012. The entire text of the aforementioned applications is incorporated herein by reference in its entirety.

The invention relates to a compound of formula (A) or a salt thereof for depigmenting the skin and/or the skin appendages.

The color of human skin and of its appendages (hair, nails, body hair, etc) depends on the phototype of the individual. A simple classification based on the strength of the constituent pigmentation (skin, hair and eye color) combined with the sensitivity to sunlight and with the ability to tan of individuals was proposed in 1975 by Dr. Fitzpatrick. The strength of the constituent pigmentation is modified by various factors, including the seasons of the year and the degree of sunshine, sex and age. It is principally determined by the concentration of melanin produced by melanocytes. Melanocytes are specialized cells which synthesize melanin by means of specific organelles, melanosomes.

Skin hyperpigmentation is a frequent disorder which manifests itself through the appearance of brown spots on the skin. It is due to a nonuniform accumulation of melanin in the skin. The pigmented spots can appear on any part of the body, in particular on the back of the hands, the face, the neckline and bald heads.

Several factors can contribute to the development of hyperpigmented lesions; the most common are genetic predisposition (Asian skin is more subject to hyperpigmented spots than caucasian skin), hormones (pregnancy mask, for example), exposure to sunlight (which causes photoaging) and skin aging. Melanin production can also be increased by a cutaneous inflammatory process, for example after a trauma, inflammatory eruptions or other phenomena, such as skin irritations.

A common form of hyperpigmentation is made up of age spots or sun spots (solar lentigo). They are due to the damage caused by the sun and generally appear on the back of the hands and of the arms, on the neckline or on the face. These spots are darker than freckles or ephelides, and persist in winter.

There is therefore a real need for an effective, risk-free treatment for hyperpigmented spots. Conversely, hypopigmentary diseases exist which are characterized by localized white maculae. Vitiligo is the most common of the hypomelanoses. The objective of the therapeutic approach is then to reduce the unattractive contrast of the affected skin compared with the normally pigmented skin, either by repigmenting the affected skin, or by depigmenting the unaffected skin. The choice of the therapeutic strategy would depend on the location and the extent of the depigmented areas. Thus, when the vitiligo is extremely widespread, it becomes fanciful to try to repigment it, and it is therefore judicious to make the skin color uniform by depigmenting the residual healthy skin. The current results are encouraging but insufficient; there is therefore a real need to identify bioactive molecules.

Finally, in Africa, in particular in North African countries, Middle Eastern countries, in the West Indies, on the American continent (United States of America, South America, Central America), in Asia (India, Philippines) and in Europe, among the populations originating from these countries, a lightening of the natural color of the skin is often perceived as a sign of social success, of respect and of better living conditions. This societal pressure results in the use of depigmenting cosmetics to obtain a lighter skin color. However, and despite the number of available products which have depigmenting properties, few can be used in cosmetology owing to their toxicity. There is therefore a real need to identify bioactive molecules that can be used entirely safely.

In this regard, numerous chemical active agents have been proposed, such as hydroquinone, retinoic acid or azelaic acid. Excellent results are admittedly obtained with the solutions proposed in the prior art, but it nevertheless remains the case that the discovery of substances which have an effect on the pigmentation of the skin or of its appendages remains a major objective of the research in this field.

This is because the prior art products must often be used with care owing to possible toxic effects. They are, moreover, increasingly monitored, or even prohibited in certain countries, such as, for example, hydroquinone, which is now banned from the formulation of cosmetic products in the European Union since regulation (EC) No. 1223/2009 of 30 Nov. 2009.

Surprisingly, the inventors have now discovered that certain lichen-derived compounds inhibit the pigmentation of the skin or of its appendages.

Application FR 2 957 078, filed by the applicants, describes the use of paraconic acids, and in particular of a mixture of protolichesterinic acid or salts, diastereoisomers or derivatives thereof, and of lichesterinic acid or salts, enantiomers or derivatives thereof, in a specific ratio, as pigmentation activators.

Among the derivatives are compounds of defined chemical formula.

As it happens, it appears that some of these compounds, used alone in vitro, at a concentration below the dose of 5 μM initially evaluated and, in addition, in a specific optical form, surprisingly have a depigmenting activity.

Thus, the subject of the invention is the cosmetic use of a compound chosen from the compounds of following formula (A) and salts thereof, in their dextrorotatory (+) form:

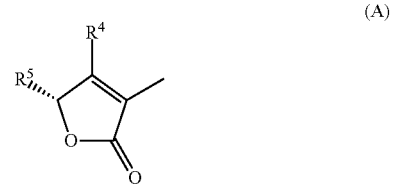

in which $R^4$ represents a hydrogen atom, an n-butyl radical, an unsubstituted phenyl radical, an unsubstituted phenethyl radical or a COOR group, where R=Na, H, methyl or ethyl, and $R^5$ is chosen from a hydrogen atom, a linear or branched $C_1$ to $C_{13}$ alkyl radical, $CH_2CCH$, Ph, $PhCH_2$, $PhCH_2CH_2$, a (linear $C_3$ to $C_{12}$ alkyl)-$CF_3$ radical, a linear $C_2$ to $C_{13}$ alkyl radical with an unsaturation, in the terminal or non-terminal position, and $(CH_2)_{13}COR^6$ where $R^6$=$OCH_3$, OH or $CH_3$, as an agent for depigmenting the skin and/or the appendages.

The subject of the invention is also a compound chosen from the compounds of following formula (A) and salts thereof, in their dextrorotatory (+) form:

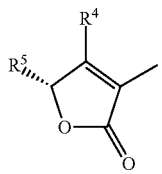

(A)

in which $R^4$ represents a hydrogen atom, an n-butyl radical, an unsubstituted phenyl radical, an unsubstituted phenethyl radical or a COOR group, where R=Na, H, methyl or ethyl, and $R^5$ is chosen from a hydrogen atom, a linear or branched $C_1$ to $C_{13}$ alkyl radical, $CH_2CCH$, Ph, $PhCH_2$, $PhCH_2CH_2$, a (linear $C_3$ to $C_{12}$ alkyl)-$CF_3$ radical, a linear $C_2$ to $C_{13}$ alkyl radical with an unsaturation, in the terminal or non-terminal position, and $(CH_2)_{13}COR^6$ where $R^6$=$OCH_3$, OH or $CH_3$, for use in depigmenting the skin and/or the appendages.

The subject of the invention is also a compound chosen from the compounds of formula (A) and salts thereof, in their dextrorotary (+) form:

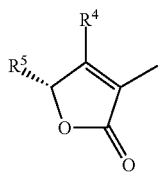

(A)

in which $R^4$ represents a hydrogen atom, an n-butyl radical, an unsubstituted phenyl radical, an unsubstituted phenethyl radical or a COOR group, where R=Na, H, methyl or ethyl, and $R^5$ is chosen from a (linear $C_3$ to $C_{12}$ alkyl)-$CF_3$ radical and a linear $C_2$ to $C_{13}$ alkyl radical with an unsaturation, in the terminal or non-terminal position.

Preferably, said compound is used as a medicament.

The subject of the invention is also a compound chosen from the compounds of following formula (A) and salts thereof, in their levorotatory (−) form, in which $R^4$ is as previously described and $R^5$ is a linear or branched $C_1$ to $C_5$ alkyl radical, and also the uses described above of these compounds.

Preferably, the $R^5$ radical with a non-terminal unsaturation is the cis-$C_2H_5CHCHC_5H_{10}$ radical.

The term "appendages" is intended to mean in particular the hair, the body hair and the nails.

Among the compounds of formula (A) is (+)-lichesterinic acid, i.e. for which $R^4$ is the COOH group, and $R^5$ is the linear alkyl radical $C_{13}H_{27}$.

In the present application, the term "lichesterinic acid" is intended to mean (+)-lichesterinic acid.

(+)-Lichesterinic acid is in fact paraconic acid (i.e. having an α-methylene-γ-lactone ring β-substituted with an acid function) of following formula (I):

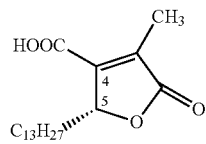

(I)

This compound is extracted from lichens, and in particular from the lichen *Cetraria islandica* Ach. or Iceland lichen.

(+)-Lichesterinic acid is in the 5R configuration by virtue of the asymmetric carbon in position 5 of the ring; the double bond is of endo type.

Among the (+)-lichesterinic acid-producing lichens are the following lichens: *Cetraria islandica, ericetorum, chlorophylla, cucullata, sepincola, ciliaris, laureri, nigricans, orbata, australiensis* or *aculeata; Cetraria komarovii* (or *Nephromopsis komarovii*); *Parmelia camtschadalis* and *Nephromopsis stracheyi* (or *Cetraria stracheyi* f *ectocarpisma*).

(+)-Lichesterinic acid can be extracted from said lichens, in particular by means of the protocol described in Horhant, D.; Le Lamer, A.-C.; Boustie, J.; Uriac, P.; Gouault, N. "*Separation of a mixture of paraconic acids from Cetraria islandica (L.) Ach. employing a fluorous tag catch and release strategy.*" Tetrahedron Lett. 2007, 48, 6031-6033.

The term "salts" of the compounds of formula (A), and in particular of lichesterinic acid, is intended to mean the salts of these compounds with alkali metals such as sodium, potassium or lithium, but also the salts of these compounds with ammonium ions.

In the present invention, unless otherwise mentioned, the term "linear or branched $C_1$ to $C_{13}$ alkyl radical" is intended to mean the methyl, ethyl, isopropyl, n-propyl, n-butyl, i-butyl or t-butyl radical, the —$C_5H_{11}$ (pentyl) radical, the —$C_9H_{19}$ (nonyl) radical or the —$C_{13}H_{27}$ (tridecyl) radical. Preferably, the linear or branched $C_1$ to $C_{13}$ alkyl radical is chosen from the n-butyl radical, the —$C_5H_{11}$ radical, the —$C_9H_{19}$ radical and the —$C_{13}H_{27}$ radical. In the present invention, unless otherwise mentioned, the term "linear or branched $C_1$ to $C_5$ alkyl radical" is intended to mean the methyl, ethyl, isopropyl, n-propyl, n-butyl, i-butyl or t-butyl radical or the —$C_5H_{11}$ (pentyl) radical.

In the present invention, unless otherwise mentioned, the term "(linear $C_3$ to $C_{12}$ alkyl)-$CF_3$ radical" is intended to mean a linear alkyl radical having from 3 to 12 carbon atoms, the terminal carbon atom being substituted with a $CF_3$ group.

In the present invention, unless otherwise mentioned, the term "linear $C_2$ to $C_{13}$ alkyl radical with an unsaturation, in the terminal or non-terminal position" is intended to mean a linear alkyl radical having from 2 to 13 carbon atoms, having an unsaturation in the terminal position. In the non-terminal position it is preferably the cis-$C_2H_5CHCHC_5H_{10}$ radical.

Preferably, the compound of formula (A) is such that $R^4$ is the COOH group, and $R^5$ is a linear or branched $C_1$ to $C_{13}$ alkyl radical.

Preferably, the compound of formula (A) is chosen from (+)-lichesterinic acid, (+)-3-methyl-5-nonylparaconic acid and (+)-3-methyl-5-pentylparaconic acid.

The compound according to the invention is used to inhibit the pigmentation of the skin and/or of the appendages. Preferably, the compound according to the invention is used to treat hyperpigmentary disorders.

The term "hyperpigmentary disorders" is intended to mean preferably the pregnancy mask, solar lentigo, photoaging and spots due to a skin inflammation, a burn or a skin irritation.

Preferably, the compound according to the invention is also used to treat hypomelanoses such as vitiligo, where the healthy skin will then be the target.

Finally, the compound according to the invention may be suitable for cosmetic use aimed at obtaining an overall bleaching of pigmented skin, in order to satisfy a societal cosmetic pressure.

The compound according to the invention can be applied to the skin or the appendages by means of a composition. Said composition preferably comprises an amount of between 0.0001% and 10% by weight relative to the total weight of the composition, preferably of between 0.5% and 5% by weight, of compound according to the invention.

The compound according to the invention can be administered by means of a composition, orally, systemically or topically by application to the skin and/or the appendages.

According to the mode of administration, the composition comprising the compound according to the invention may be in any of the pharmaceutical forms.

Preferably, the compound according to the invention is included in a composition which is administered topically to the skin and/or the appendages.

For oral administration, the compositions may be in the form of tablets, gel capsules, sugar-coated tablets, syrups, suspensions, solutions, powders, granules, emulsions, or microspheres or nanospheres or lipid or polymeric vesicles for controlled release.

For topical application to the skin, the composition may be in the form in particular of an aqueous or oily solution or of a dispersion of the lotion or serum type; of an emulsion of liquid or semi-liquid consistency of the milk type, obtained by dispersion of a fatty phase in an aqueous phase (O/W) or vice versa (W/O); of an emulsion of soft consistency of the cream type; of a two-phase emulsion; of an aqueous or anhydrous gel; of a foam or else of microcapsules or microparticles, or of vesicular dispersions of ionic and/or nonionic type, or else of spray formulae. These compositions are prepared according to the usual methods known to those skilled in the art.

For topical application to the hair, the composition may be in the form of aqueous, alcoholic or aqueous-alcoholic solutions; of gels; of emulsions; of foams; or else in the form of aerosol compositions also comprising a pressurized propellant. The composition according to the invention may also be a hair care composition, and in particular a shampoo, a treating lotion, a styling cream or gel, or else a lotion or a gel for combating hair loss.

For systemic application, the composition may be in the form of an aqueous or oily solution or in the form of a serum.

The composition comprising the compound according to the invention may in particular comprise a fatty phase, an emulsifier, a solvent, a propenetrating agent or else a gelling agent (which is lipophilic or hydrophilic).

When the composition comprises a fatty phase, the latter comprises at least one oil or one wax. As oils or waxes that can be used in the invention, mention may be made of mineral oils (liquid petroleum jelly), vegetable oils (liquid fraction of shea butter, sunflower oil), animal oils (perhydrosqualene), synthetic oils (purcellin oil), silicone oils or waxes (cyclomethicone), fluoro oils (perfluoropolyethers), beeswax, carnauba wax or paraffin wax, and also fatty alcohols and fatty acids (stearic acid).

The composition may also comprise at least one emulsifier. This emulsifier may be anionic, cationic, nonionic or amphoteric.

As solvents that can be used according to the invention, mention may be made of lower alcohols, in particular ethanol and isopropanol, and propylene glycols.

As propenetrating agents that can be used according to the invention, mention may be made of glycols, in particular 1,2-propanediol (or propylene glycol) and polyethylene glycols.

As hydrophilic gelling agents that can be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, mention may be made of modified clays such as bentones, metal salts of fatty acids, such as aluminum stearates, and hydrophobic silica, ethylcellulose and polyethylene.

According to the invention, the composition may combine the compound according to the invention with other active agents.

Among these active agents, mention may be made, by way of example of:

depigmenting agents, such as retinoids, azelaic acid or kojic acid;

agents which improve hair restoring activity and/or activity for slowing down hair loss, and which have already been described for this activity, for example minoxidil, aminexil, nicotinic acid esters, including in particular tocopheryl nicotinate, benzyl nicotinate and $C_1$-$C_6$ alkyl nicotinates, for instance methyl or hexyl nicotinates;

steroidal anti-inflammatory agents, such as hydrocortisone, betamethasone valerate or clobetasol propionate;

antifungal agents, such as ketoconazole, selenium sulfide, itraconazole or fluconazole; or antipruritic agents, for instance thenaldine, trimeprazine or cyproheptadine.

The composition may also comprise conventional adjuvants, such as preservatives, antioxidants, fragrances, fillers, odor absorbers and colorants.

The amounts of these various adjuvants are those conventionally used, and are for example from 0.01% to 20% by weight relative to the total weight of the composition.

Several processes will be envisioned depending on the nature of the $R^4$ and $R^5$ radicals of the compounds of formula (A). The process below describes the enantioselective synthesis of the compounds of formula (A) with $R^4$=COOH.

This process is derived, for steps a, b, c and f, from a publication by S. Braukmüller and R. Brückner, *Eur. J. Org. Chem.* 2006, 2110-2118.

It is an enantioselective synthesis in 7 steps, in which enantiocontrol is provided by steps b and d. The condensation of the aldehyde on methyl hydrogeno malonate (step a) results in a trans-unsaturated carboxylic ester. A Sharpless asymmetric dihydroxylation makes it possible to obtain an enantiopure hydroxy-lactone (step b). After dehydratation (step c) and selective trans-addition of the vinyl group (step d), the compound is converted into paraconic acid (step e). -activation in the presence of methyl magnesium carbonate followed by decarboxylative methylenation produces the derivative of (+) or (−)-protolichesterinic acid (step f). Isomerization of the exo double bond to endo gives derivatives of formula A (step g).

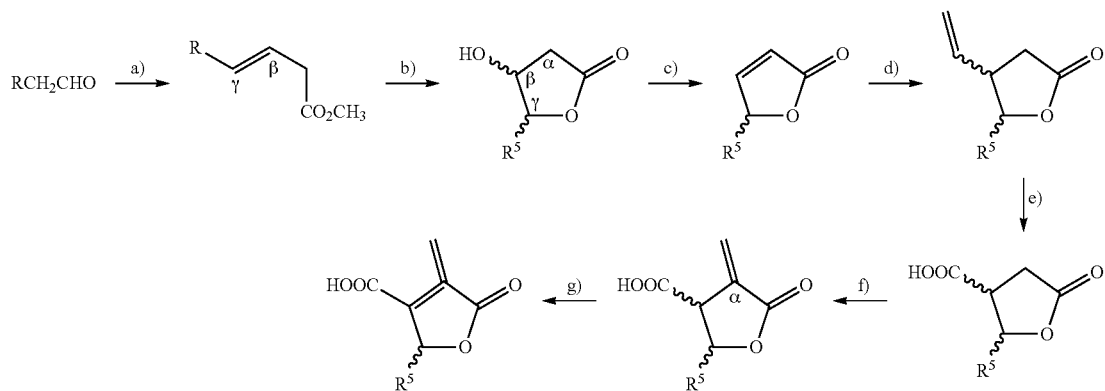

a) HOOCCH₂CO₂C₂H₅ (1.0 eq), NEt₃ (1.0 eq), 90° C., 3 h; b) AD mix-® or AD mix-®, MeSO₂NH₂ (1.0 eq), tBuOH/H₂O (1:1), 0° C., 40 h;
c) MsCl (1.1 eq), NEt₃ (2.1 eq), CH₂Cl₂, 0° C., 15 min; d) CuI (10 eq), THF, -78° C., MeLi (10 eq), 15 min; vinylmagnesium bromide (10 eq),
15 min, addition of furanone, 2 h; e) NaIO₄ (4.0 eq), RuCl₃ (0.1 eq), CCl₄/CH₃CN/H₂O (2:2:3), AT 3 h; f) (i) MeOMg[O(C=O)Ome] (38 eq) in
DMF, 135-140° C., 70 h, isolation of the crude product; (ii) crude product, HOAc/NaOAc/formalin (=35-40% acqueous solution of formaldehyde)/
N-methylaniline (excess; 4:0.03:3:1), AT, 2 h; g) NEt₃, DMF, 18 h.

Of course, those skilled in the art take care not to introduce compounds into the composition used in the present invention in such a way that said compounds counteract the desired technical effect, which is the subject of the present invention.

Examples will now be given for the purposes of illustration, which are not intended to limit the scope of the invention in any way.

The figure legends are the following:

FIG. 1: Melanin level in B16 cells relative to controls (100%) measured by absorbance after 4 days of incubation (Petri dishes) with concentrations of less than or equal to 2 µM of a (+)LA/(+)PLA/(+)RA mixture in the respective proportions 60/25/15.

Figure 2:
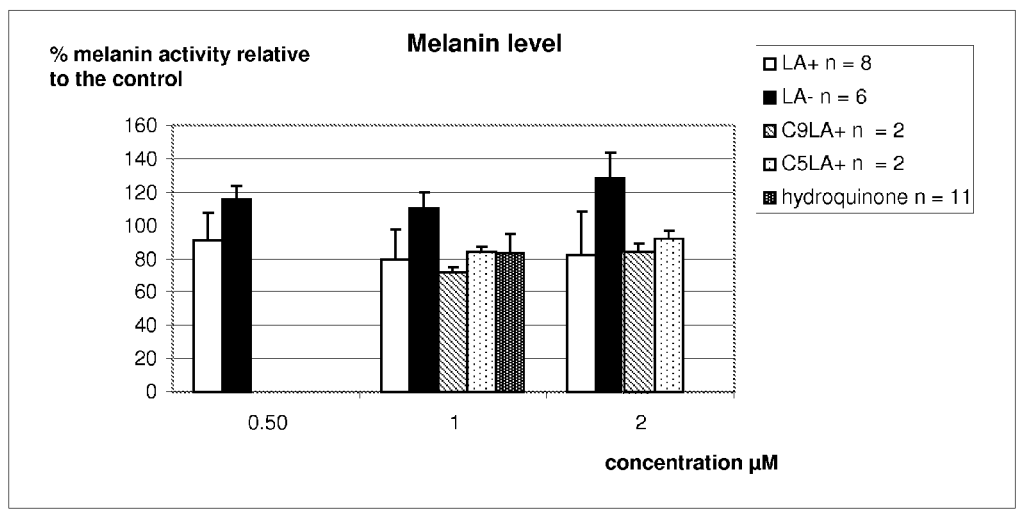

FIG. 2: Melanin level in B16 cells relative to controls (Petri dishes) measured by absorbance after 4 days of incubation at 3 concentrations of LA+ and of LA−, and at 2 concentrations of C9LA+ and C5LA+. The depigmenting positive control used is hydroquinone.

The abbreviations are the following:

(+)LA or LA+=(+)-lichesterinic acid (or dextrorotatory lichesterinic acid)
(−)LA or LA−=(−)-lichesterinic acid (or levorotatory lichesterinic acid)
(+)PLA or PLA+=(+)-protolichesterinic acid (or dextrorotatory protolichesterinic acid)
(+)RA or RA+=(+)-roccellaric acid (or dextrorotatory roccellaric acid)
C9LA+=(+)-3-methyl-5-nonylparaconic acid (or dextrorotatory 3-methyl-5-nonylparaconic acid)
C5LA+=(+)-3-methyl-5-pentylparaconic acid (or dextrorotatory 3-methyl-5-nonylparaconic acid)
and correspond to the following formulae:

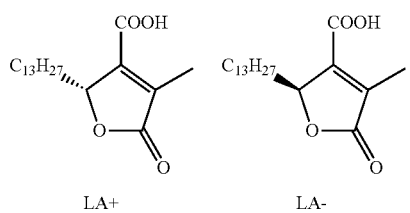

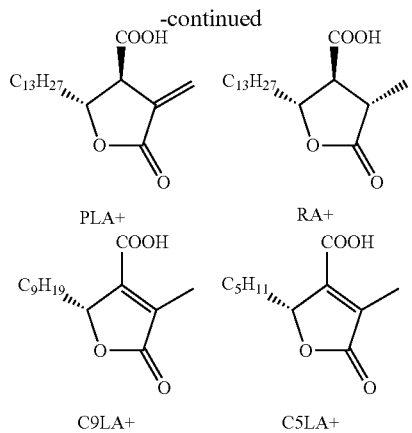

EXAMPLE 1

Demonstration of the In Vitro Depigmenting Activity of (+)-Lichesterinic Acid ((+)LA)

Protocol: The melanin content of murine B16 cells is determined by spectrophotometry, and all the concentrations retained for the tests do not exhibit, under the conditions described, any cell toxicity (B16 viability >80%).

The cells are seeded in a 10 cm Petri dish at a density of $7 \times 10^5$ per dish and are incubated for 96 hours, with a defined concentration of lichen-derived molecule, which has been purified and solubilized in DMSO. After treatment, the cells are recovered by treatment with trypsin and washed twice with PBS. The number of cells recovered is estimated by counting using a hemocytometer. One and the same fraction is used to determine the melanin content and the protein concentration. The melanin content is determined by the absorbance at 405 nm (VersaMax Microplate Reader, Molecular Devices, USA) of the cell solution after solubilization of the melanin with 1M sodium hydroxide, for 15 min at 80° C. The protein concentration is determined according to the protocol of the "DC Protein Assay" kit developed by Bio-Rad laboratories, USA. For each sample treated, the melanin content is related to the amount of protein and expressed as a percentage relative to the control situation (DMSO solution alone). Each measurement is carried out in triplicate and each experiment is carried out independently a minimum of 3 times (except for the C9LA+ and C5LA+ derivatives given by way of indication).

FIGS. 1 and 2 bring together the results. These figures show the melanin content of the B16 cells treated for 96 h in the presence of a given molecule (FIG. 2), or of a (+)-lichesterinic acid ((+)LA)/(+)-protolichesterinic acid ((+)PLA)/(+)-roccellaric acid ((+)RA) mixture in a 60/25/15 weight ratio (FIG. 1).

Along the x-axis are the molecules tested with their concentrations expressed in μM.

Along the y-axis, the melanin content is expressed as a percentage relative to the control (DMSO alone=concentration of 0.1%).

The results of FIG. 1 show that, for a mixture containing (+)-lichesterinic acid, (+)-protolichesterinic acid and (+)-roccellaric acid in the respective proportions 60/25/15, an inhibition of about −20% to −50% of the melanin level is recorded at the concentrations of 1 and 2 μM.

The results of FIG. 2 show, for their part, that the two enantiomers of lichesterinic acid give opposite activities, that is to say +10% to +30% stimulation of melanin production for (−)-lichesterinic acid (LA−) at concentrations of 0.5 to 2 μM, and 10% to 20% decrease in the melanin level for (+)-protolichesterinic acid (PLA+) at the same concentrations.

Compared with the depigmenting positive control (hydroquinone, which induces a decrease of −20% in the melanin level under the same conditions), (+)-lichesterinic acid, (+)-3-methyl-5-nonylparaconic acid (C9LA+) and (+)-3-methyl-5-pentylparaconic acid (C5LA+) exhibit a comparable depigmenting activity (in the case of C5×LA+) or a greater depigmenting activity.

At the same time, other results not given here indicate that, for the other 2 constituent products of the mixture, which are individually isolated, the tests under the same conditions result in a decrease in the melanin level which is about −20% for (+)-protolichesterinic acid at 0.25 μM, and which is not significant for roccellaric acid at 1 μM, their respective enantiomers having, themselves also, the same level of activity at these same concentrations.

The results obtained therefore demonstrate the depigmenting activity of (+)-lichesterinic acid and of its derivatives according to the invention.

The invention claimed is:

1. A method of depigmenting the skin and/or the appendages comprising
   administering a compound chosen from (+)-lichesterinic acid, (+)-3-methyl-5-nonylparaconic acid and (+)-3-methyl-5-pentylparaconic acid, and salts thereof.

2. The method of claim 1 wherein the compound or salt thereof, in dextrorotatory form, is present in an amount of between 0.0001% and 10% by weight relative to the total weight of the composition.

* * * * *